United States Patent
Shida et al.

(10) Patent No.: US 9,392,942 B2
(45) Date of Patent: Jul. 19, 2016

(54) FLUOROSCOPY APPARATUS AND FLUOROSCOPY SYSTEM

(71) Applicant: OLYMPUS CORPORATION, Tokyo (JP)

(72) Inventors: Hiromi Shida, Tokyo (JP); Yasushige Ishihara, Tokyo (JP); Satoshi Takekoshi, Tokyo (JP); Kei Kubo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 349 days.

(21) Appl. No.: 13/952,954

(22) Filed: Jul. 29, 2013

(65) Prior Publication Data
US 2014/0037179 A1 Feb. 6, 2014

(30) Foreign Application Priority Data
Aug. 1, 2012 (JP) ................................. 2012-171181

(51) Int. Cl.
*G01T 1/161* (2006.01)
*A61B 5/00* (2006.01)
(Continued)

(52) U.S. Cl.
CPC .............. *A61B 5/0033* (2013.01); *A61B 1/0005* (2013.01); *A61B 1/00009* (2013.01);
(Continued)

(58) Field of Classification Search
CPC .. A61B 1/043; A61B 1/00009; A61B 1/0005; A61B 1/00055; A61B 5/0033; G06T 5/50; G06T 2207/10064; G06T 2207/10121; G06T 2207/20212; G06T 2207/30088; G06T 7/0014

USPC ....................... 250/363.09; 382/132
See application file for complete search history.

(56) References Cited

U.S. PATENT DOCUMENTS

| 8,472,749 | B2 * | 6/2013 | Watanabe | ............ | A61B 1/0638 |
| | | | | | 382/128 |
| 2005/0267340 | A1 * | 12/2005 | Ishihara | ............... | A61B 5/0062 |
| | | | | | 600/310 |

(Continued)

FOREIGN PATENT DOCUMENTS

| JP | 2006-014924 A | 1/2006 |
| JP | 2006-191989 A | 7/2006 |

(Continued)

OTHER PUBLICATIONS

Japanese Office Action dated May 10, 2016 in Japanese Patent Application No. 2012-171181.

*Primary Examiner* — David J Makiya
*Assistant Examiner* — Taeho Jo
(74) *Attorney, Agent, or Firm* — Scully, Scott, Murphy & Presser, PC

(57) ABSTRACT

Provided is a fluoroscopy apparatus including a light source that irradiates an observation target with reference light and excitation light; a fluorescence-image generating unit that captures fluorescence emitted from the observation target X irradiated with the excitation light to generate a fluorescence image; a reference-image generating unit that captures return light returning from the observation target irradiated with the reference light to generate a reference image; an image-combining unit that superimposes the fluorescence image on the reference image to generate a combined image; a determining unit that determines whether there is a position with a luminance at or below a predetermined threshold in the reference image; and a notifying unit that, if the determining unit determines that there is a position with a luminance at or below the predetermined threshold, provides notification thereof.

14 Claims, 10 Drawing Sheets

(51) Int. Cl.
*A61B 1/00* (2006.01)
*G06T 5/50* (2006.01)
*G06T 7/00* (2006.01)
*A61B 1/04* (2006.01)

(52) U.S. Cl.
CPC .............. *A61B1/00055* (2013.01); *G06T 5/50* (2013.01); *G06T 7/0014* (2013.01); *A61B 1/043* (2013.01); *G06T 2207/10121* (2013.01); *G06T 2207/30088* (2013.01)

(56) References Cited

U.S. PATENT DOCUMENTS

| | | | | |
|---|---|---|---|---|
| 2008/0075348 | A1* | 3/2008 | Rappaport | A61B 5/107 382/132 |
| 2010/0245550 | A1* | 9/2010 | Ishihara | A61B 1/0638 348/68 |
| 2010/0245619 | A1* | 9/2010 | Watanabe | A61B 1/043 348/226.1 |
| 2011/0313297 | A1* | 12/2011 | Ishihara | A61B 1/00057 600/477 |
| 2012/0007001 | A1* | 1/2012 | Ishihara | A61B 1/00057 250/459.1 |
| 2012/0076434 | A1* | 3/2012 | Watanabe | A61B 1/0638 382/274 |
| 2012/0123205 | A1* | 5/2012 | Nie | A61B 1/00174 600/109 |
| 2012/0319006 | A1* | 12/2012 | Shida | A61B 1/043 250/458.1 |
| 2013/0003922 | A1* | 1/2013 | Watanabe | A61B 1/00009 378/42 |
| 2013/0039562 | A1* | 2/2013 | Watanabe | A61B 1/043 382/132 |
| 2013/0177972 | A1* | 7/2013 | Green | C12M 21/08 435/288.7 |

FOREIGN PATENT DOCUMENTS

| | | | | |
|---|---|---|---|---|
| JP | WO 2011115095 A1 * | 9/2011 | | A61B 1/00009 |
| JP | 2011-217886 A | 11/2011 | | |

* cited by examiner

US 9,392,942 B2

FLUOROSCOPY APPARATUS AND FLUOROSCOPY SYSTEM

CROSS-REFERENCE TO RELATED APPLICATIONS

This application claims the benefit of Japanese Patent Application No. 2012-171181, the content of which is incorporated herein by reference.

TECHNICAL FIELD

The present invention relates to fluoroscopy apparatuses and fluoroscopy systems.

BACKGROUND ART

There are known fluoroscopy apparatuses in the related art that extract a fluorescence region with a higher signal level than the surrounding region as an affected area from a fluorescence image acquired from body tissue and that notify the user that there is an affected area (see, for example, PTL 1).

CITATION LIST

Patent Literature

{PTL 1}
Japanese Unexamined Patent Application, Publication No. 2006-191989

SUMMARY OF INVENTION

A first aspect of the present invention is a fluoroscopy apparatus including a light source that irradiates an observation target with reference light and excitation light; a fluorescence-image generating unit that captures fluorescence emitted from the observation target irradiated with the excitation light from the light source to generate a fluorescence image; a reference-image generating unit that captures return light returning from the observation target irradiated with the reference light from the light source to generate a reference image; an image-combining unit that superimposes the fluorescence image generated by the fluorescence-image generating unit on the reference image generated by the reference-image generating unit to generate a combined image; a determining unit that compares a luminance at each position in the reference image generated by the reference-image generating unit with a predetermined threshold to determine whether there is a position with a luminance at or below the predetermined threshold; and a notifying unit that, if the determining unit determines that there is a position with a luminance at or below the predetermined threshold, provides notification thereof.

A second aspect of the present invention is a fluoroscopy system including the above fluoroscopy apparatus and a calibration device that calibrates the detection limit threshold used by the determining unit. The calibration device includes a standard sample that emits fluorescence and return light when irradiated with the excitation light and the reference light from the light source; a light-intensity adjusting unit that changes the intensities of the excitation light and the reference light with which the standard sample is irradiated; and a threshold-determining unit that determines the detection limit threshold based on the relationship between the luminances of a plurality of reference images and a plurality of fluorescence images generated by capturing fluorescence and return light when the standard sample is irradiated with excitation light and reference light with different intensities by the light-intensity adjusting unit and that sets the detection limit threshold in the determining unit.

DESCRIPTION OF EMBODIMENTS

A fluoroscopy apparatus 1 according to an embodiment of the present invention will be described below with reference to FIGS. 1 to 10.

Figure 1:
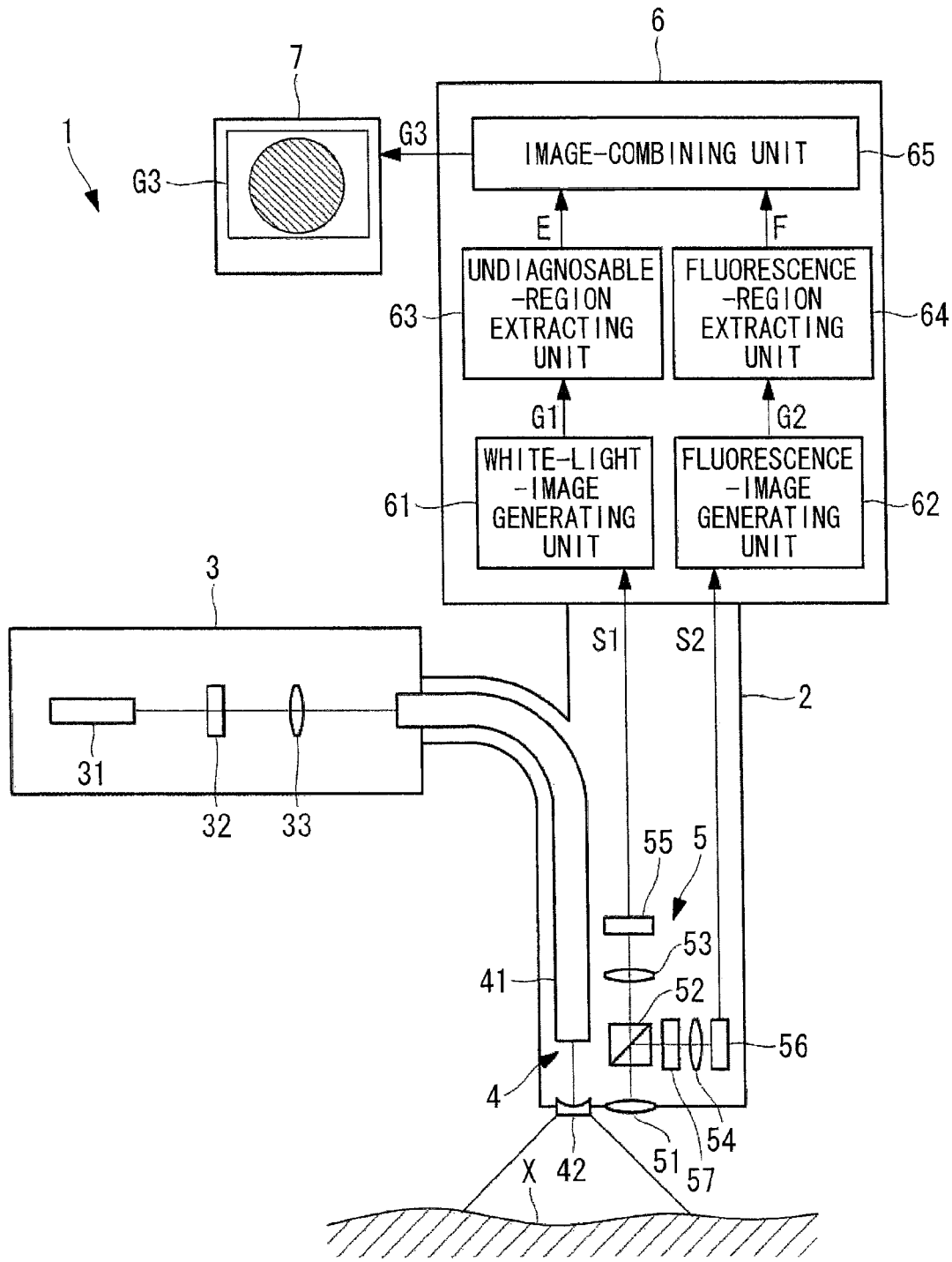
FIG. 1 is an overall block diagram showing a fluoroscopy apparatus according to an embodiment of the present invention.

As shown in FIG. 1, the fluoroscopy apparatus 1 according to this embodiment is an endoscope apparatus including an elongated insertion part 2 for insertion into the body; a light source 3; an illumination unit 4 that directs excitation light and white light emitted from the light source 3 onto an observation target X from a distal end 2a of the insertion part 2; an imaging unit 5 that is disposed at the distal end 2a of the insertion part 2 and that acquires image information S1 and S2 for the observation target X, i.e., body tissue; an image processor 6 that is disposed at the proximal end of the insertion part 2 and that processes the image information S1 and S2 acquired by the imaging unit 5; and a display 7 that displays an image G processed by the image processor 6.

The light source 3 includes a xenon lamp 31, a filter 32 that extracts excitation light and white light (illumination light, wavelength range: 400 to 740 nm) from light emitted from the xenon lamp 31, and a coupling lens 33 that condenses the excitation light and the white light extracted by the filter 32.

The illumination unit 4 includes a light-guide fiber 41 disposed substantially over the entire length of the insertion part 2 in the longitudinal direction and an illumination optical system 42 disposed at the distal end 2a of the insertion part 2. The light-guide fiber 41 guides the excitation light and the white light condensed by the coupling lens 33. The illumination optical system 42 spreads out the excitation light and the white light guided by the light-guide fiber 41 onto the observation target X, which faces the distal end 2a of the insertion part 2.

The imaging unit 5 includes an objective lens 51 that collects light returning from a predetermined observation region of the observation target X; a dichroic mirror 52 that reflects light (excitation light and fluorescence) with wavelengths longer than or equal to the excitation wavelength and transmits white light (return light) with wavelengths shorter than the excitation wavelength in the light collected by the objective lens 51; a condenser lens 53 that condenses the white light transmitted by the dichroic mirror 52; a condenser lens 54 that condenses the fluorescence reflected by the dichroic mirror 52; an imaging device 55, such as a CCD sensor, that acquires an image of the white-light condensed by the condenser lens 53; and an imaging device 56, such as a CCD sensor, that acquires an image of the fluorescence condensed by the condenser lens 54.

The imaging devices 55 and 56 acquire white-light image information S1 and fluorescence image information S2 at a predetermined frame rate.

As shown, reference sign 57 denotes an excitation-light-cut filter that blocks the excitation light in the light reflected by the dichroic mirror 52 (for example, transmits only light in the wavelength range of 760 to 850 nm).

The image processor 6 includes a white-light-image generating unit (reference-image generating unit) 61 that generates a white-light image (reference image) G1 from the white-light image information S1 acquired by the imaging device 55; a fluorescence-image generating unit 62 that generates a fluorescence image G2 from the fluorescence image information S2 acquired by the imaging device 56; an undiagnosable-region extracting unit (determining unit, extracting unit) 63 that extracts pixels with luminances at or below a predetermined detection limit threshold from the white-light image G1; a fluorescence-region extracting unit 64 that extracts pixels with luminances at or above a predetermined fluorescence threshold from the fluorescence image G2; and an image-combining unit (notifying unit) 65 that generates a combined image G3 from the pixels extracted by the undiagnosable-region extracting unit 63 and the fluorescence-region extracting unit 64 and the white-light image G1.

Figure 4:
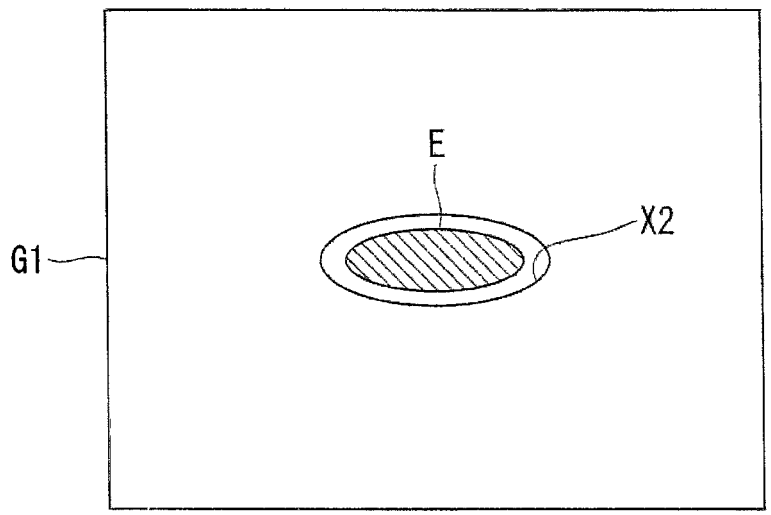
FIG. 4 is a diagram showing a white-light image generated by the fluoroscopy apparatus in FIG. 1 and an undiagnosable region extracted from the white-light image.

The undiagnosable-region extracting unit 63 compares the luminance of each pixel of the white-light image G1 input from the white-light-image generating unit 61 with the predetermined detection limit threshold and extracts a group of pixels with luminances at or below the detection limit threshold as an undiagnosable region E, as shown in FIG. 4. The detection limit threshold, described later, is determined based on the relationship between the luminances of white-light images G1 and fluorescence images G2 acquired in advance with the use of the imaging devices 55 and 56, respectively.

The fluorescence-region extracting unit 64 compares the luminance of each pixel of the fluorescence image G2 input from the fluorescence-image generating unit 62 with the predetermined fluorescence threshold and extracts a group of pixels with luminances at or above the fluorescence threshold as a fluorescence region F.

Figure 2:
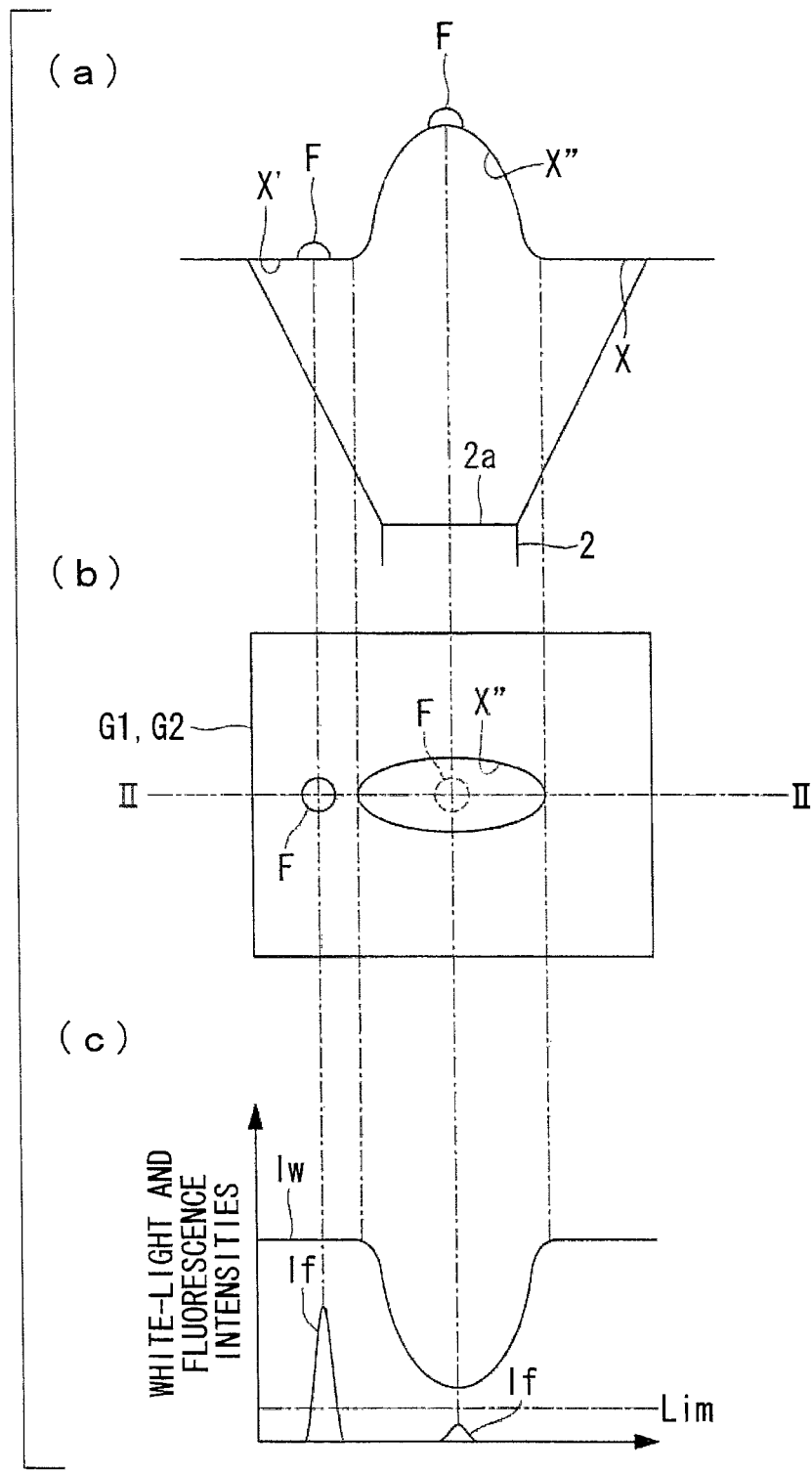
FIG. 2 is diagrams showing (a) an observation target observed using the fluoroscopy apparatus in FIG. 1, (b) a white-light image and a fluorescence image acquired from the observation target, and (c) a graph showing the white-light and fluorescence intensities detected by imaging devices.

Diagrams (a) to (c) of FIG. 2 illustrate the relationship between the profile of the observation target X, the intensity Iw of the white light and the intensity If of the fluorescence detected by the imaging devices 55 and 56, and the white-light image G1 and the fluorescence image G2 generated by the respective image-generating units 61 and 62. Diagram (a) of FIG. 2 shows the profile of the observation target X. Diagram (b) of FIG. 2 shows the white-light image G1 and the fluorescence image G2 acquired from the observation target X shown in (a) of FIG. 2 as being superimposed on top of each other. Diagram (c) of FIG. 2 shows the intensity Iw of the white light and the intensity If of the fluorescence detected by the imaging devices 55 and 56 at the position corresponding to line II-II in (b) of FIG. 2.

The intensities of the white light and the excitation light directed onto the observation target X are sufficiently high at a flat site X' or a protruding site of the observation target X closer to the distal end 2a of the insertion part 2 and are lower at a recessed site X" farther away from the distal end 2a of the insertion part 2. The white light directed onto the observation target X, however, has sufficient intensity so that the white light reflected by the observation target X and incident on the imaging device 55 has sufficient intensity Iw at the recessed site X", as shown in (c) of FIG. 2. Thus, the resulting white-light image G1 shows the entire observation target X with sufficient clarity.

The fluorescence emitted from the observation target X generally has a lower intensity than the reflected light (white light). If the flat site X' and the recessed site X" emit fluorescence with the same intensity, the fluorescence incident on the imaging device 56 from the flat site X', which is closer to the distal end 2a of the insertion part 2, has sufficient intensity If, whereas the fluorescence incident on the imaging device 56 from inside the recessed site X", which is farther away from the distal end 2a of the insertion part 2, has insufficient intensity If.

That is, as shown in (c) of FIG. 2, the intensity If of the fluorescence incident on the imaging device 56 from inside the recessed site X" falls below the detection limit Lim of the imaging device 56 for fluorescence. Such fluorescence is not detected by the imaging device 56 or, if detected, is represented as a luminance below the predetermined fluorescence threshold in the fluorescence image G2. As a result, as shown in (b) of FIG. 2, the fluorescence-region extracting unit 64 does not extract the fluorescence region F at the recessed site X".

Thus, the intensities Iw and If of the white light and the fluorescence incident on the respective imaging devices 55 and 56 from the observation target X vary in proportion to each other depending on the observation distance. When the observation distance increases, the intensity If of the fluorescence falls below the detection limit Lim of the imaging device 56 before the intensity Iw of the white light reaches the detection limit of the imaging device 55. The luminance of a white-light image G1 acquired from white light having the intensity Iw corresponding to the fluorescence intensity If equal to the detection limit Lim of the imaging device 56 is set as the detection limit threshold in the undiagnosable-region extracting unit 63.

The image-combining unit 65 generates a marker M indicating the position of the undiagnosable region E extracted by the undiagnosable-region extracting unit 63. The image-combining unit 65 then superimposes the marker M and the fluorescence region F extracted by the fluorescence-region extracting unit 64 on the white-light image G1 to generate a combined image G3 (see FIG. 6). The image-combining unit 65 outputs the resulting combined image G3 to the display 7. The marker M is, for example, hatching in the undiagnosable region E, a circle surrounding the undiagnosable region E, or an arrow.

The display 7 displays the combined image G3 input from the image-combining unit 65.

Next, the operation of the thus-configured fluoroscopy apparatus 1 will be described below.

To observe the observation target X, i.e., body tissue, using the fluoroscopy apparatus 1 according to this embodiment, the insertion part 2 is inserted into the body, and the distal end 2a of the insertion part 2 is positioned opposite the observation target X. The light source 3 is then operated to emit excitation light and white light. The excitation light and the white light are directed into the light-guide fiber 41 by the coupling lens 33, are guided through the light-guide fiber 41 to the distal end 2a of the insertion part 2, and are spread out onto the observation target X by the illumination optical system 42.

The observation target X emits fluorescence as a result of a fluorescent substance contained therein being excited by the excitation light. At the same time, the white light is reflected by the surface of the observation target X. The fluorescence and the reflected white light return from the observation target X to the distal end 2a of the insertion part 2 and are collected by the objective lens 51.

Figure 3:
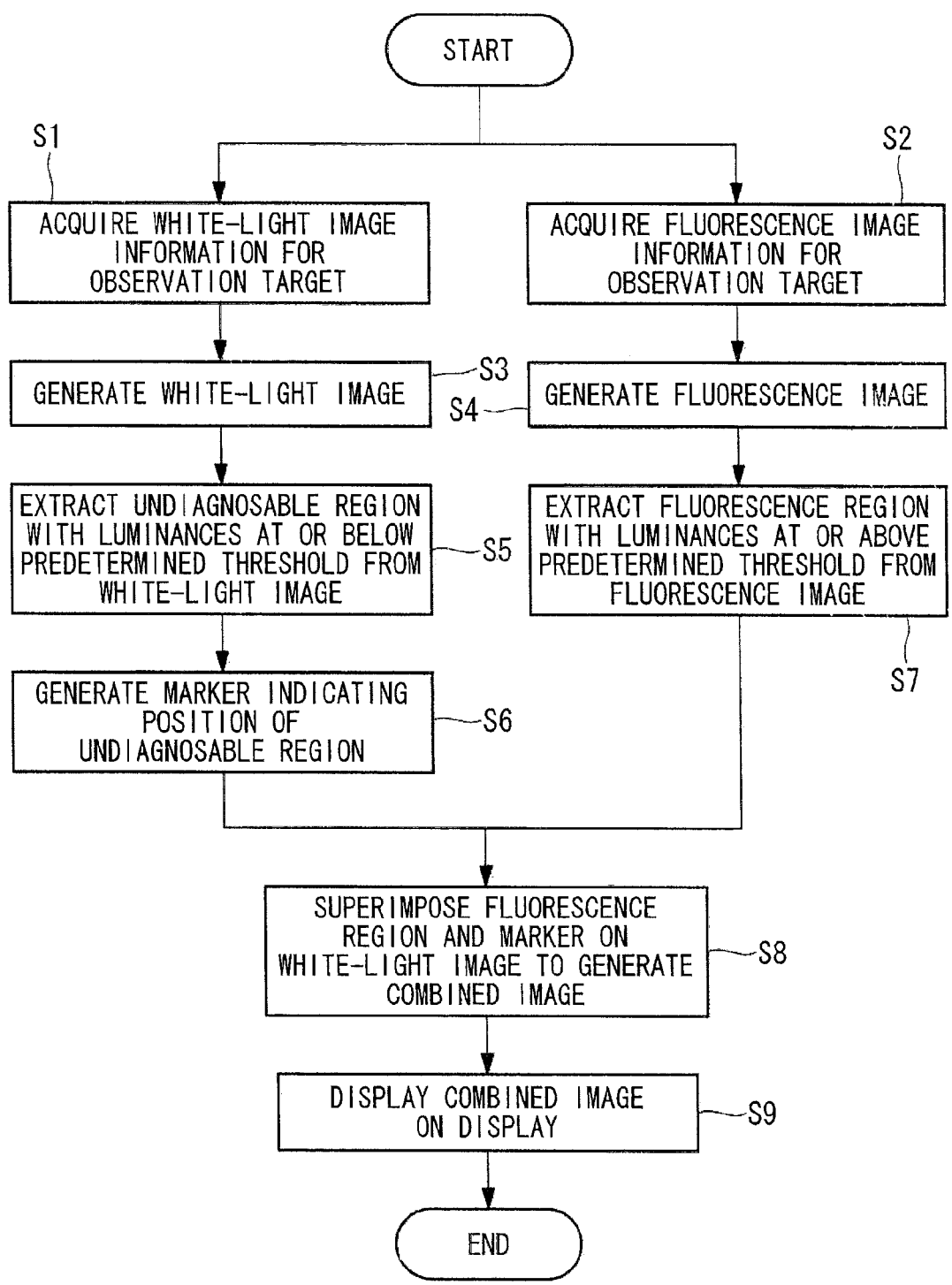
FIG. 3 is a flowchart illustrating the operation of the fluoroscopy apparatus in FIG. 1.

FIG. 3 shows a flowchart illustrating a process by which the fluoroscopy apparatus 1 according to this embodiment generates the combined image G3.

The fluorescence and the white light collected by the objective lens 51 are split into different wavelength ranges by the dichroic mirror 52. For example, white light in the wavelength range of 400 to 700 nm is condensed by the condenser lens 53 and is detected by the imaging device 55 to acquire white-light image information S1 (step S1).

Of the fluorescence and the white light collected by the objective lens 51, the light reflected by the dichroic mirror 52, which contains, for example, excitation light and fluorescence in the wavelength range of 700 to 850 nm, passes through the excitation-light-cut filter 57, which removes the excitation light (for example, light with wavelengths of 740 nm or less). The remaining fluorescence is condensed by the condenser lens 54 and is detected by the imaging device 56 to acquire fluorescence image information S2 (step S2).

The image information S1 and S2 acquired by the respective imaging devices 55 and 56 are fed to the image processor 6. The image processor 6 inputs the white-light image information S1 to the white-light-image generating unit 61, which generates a white-light image G1 (step S3), and inputs the fluorescence image information S2 to the fluorescence-image generating unit 62, which generates a fluorescence image G2 (step S4).

The resulting white-light image G1 is fed to the undiagnosable-region extracting unit 63. As shown in FIG. 4, the undiagnosable-region extracting unit 63 extracts an undiagnosable region E with luminances at or below the predetermined detection limit threshold from the white-light image G1 (step S5). The extracted undiagnosable region E is fed to the image-combining unit 65. The image-combining unit 65 generates a marker M indicating the position of the undiagnosable region E (step S6).

Figure 5:
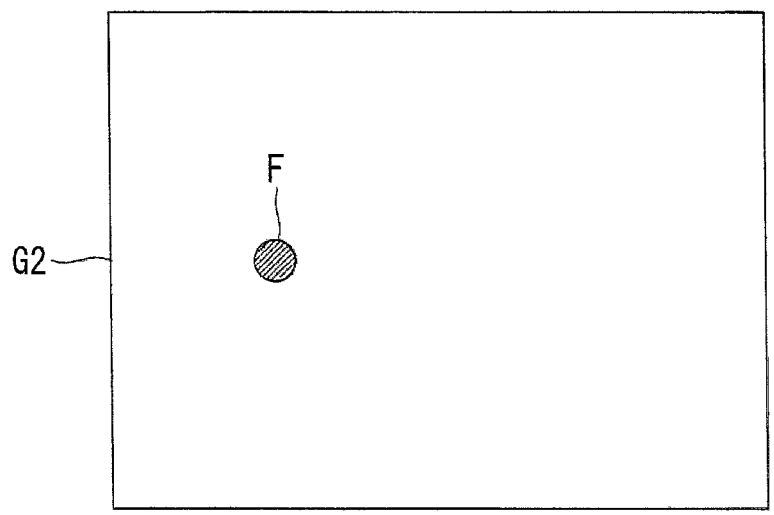
FIG. 5 is a diagram showing a fluorescence image generated by the fluoroscopy apparatus in FIG. 1 and a fluorescence region extracted from the fluorescence image.

The resulting fluorescence image G2 is fed to the fluorescence-region extracting unit 64. As shown in FIG. 5, the fluorescence-region extracting unit 64 extracts a fluorescence region F with luminances at or above the predetermined fluorescence threshold from the fluorescence image G2 (step S7). The extracted fluorescence region F is fed to the image-combining unit 65.

Figure 6:
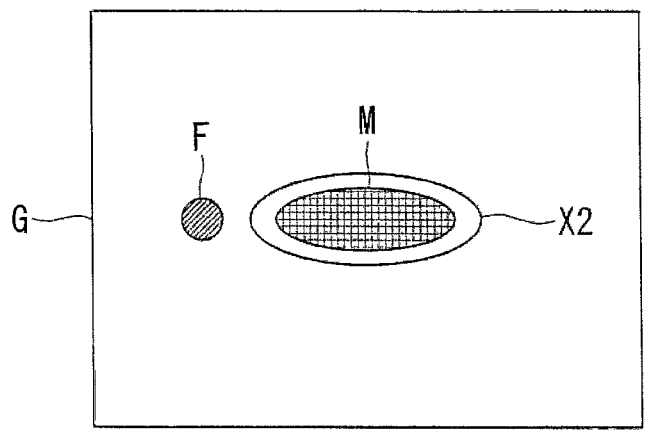
FIG. 6 is a diagram showing a combined image generated by the fluoroscopy apparatus in FIG. 1.

As shown in FIG. 6, the image-combining unit 65 superimposes the resulting marker M and fluorescence region F on the white-light image G1 to generate a combined image G3 (step S8) and outputs the combined image G3 to the display 7 (step S9). FIG. 6 shows the marker M as hatching in the entire undiagnosable region E.

If a fluorescence region F appears in the combined image G3 displayed on the display 7, the user can recognize the fluorescence region F as an affected area. If a marker M appears in the combined image G3, the user can recognize the possibility that an affected area has not been properly detected at the position indicated by the marker M and can check whether there is an affected area, for example, by bringing the distal end 2a of the insertion part 2 closer to the region indicated by the marker M to examine the region under magnification.

As described above, with the fluoroscopy apparatus 1 according to this embodiment, the undiagnosable-region extracting unit 63 extracts a dark region in the white-light image G1 where it is possible that fluorescence that has occurred has not been detected by the imaging device 56 as an undiagnosable region E. The white light intensity remains sufficiently higher than the fluorescence intensity even if they vary with varying observation conditions. The use of such white light allows the undiagnosable-region extracting unit 63 to accurately determine that there is a fluorescence region that has not been displayed at a luminance sufficient to be visible in the fluorescence image G2. The extracted undiagnosable region E is indicated by a marker M in the combined image G3. This provides the advantage of ensuring that the user can recognize the possibility of a false negative region where fluorescence that has occurred has not been displayed as a fluorescence region F in the combined image G3, thereby assisting in more accurate diagnosis by the user.

Although this embodiment illustrates the marker M as uniform hatching in the entire undiagnosable region E, a marker M showing a luminance distribution of the white-light image G1 in the undiagnosable region E using a plurality of display forms may be generated instead.

Figure 7:
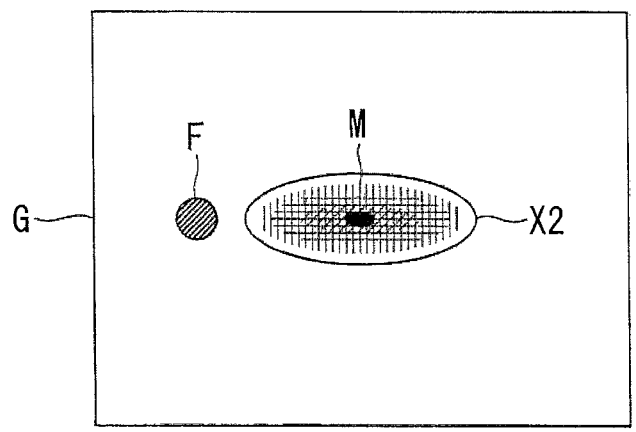
FIG. 7 is a diagram showing a modification of the combined image generated by the fluoroscopy apparatus in FIG. 1.

Specifically, the undiagnosable-region extracting unit 63 has a plurality of detection limit thresholds. The image-combining unit 65 determines to which of the ranges defined by the plurality of thresholds the luminance of each pixel with a luminance at or below the highest threshold belongs, and generates a marker M using different hatching patterns for different ranges. Thus, as shown in FIG. 7, regions with different luminances are indicated by different hatching patterns.

This allows the user to recognize the likelihood that fluorescence that has occurred has not been detected in the undiagnosable region E according to the difference in display form.

Next, a modification of the fluoroscopy apparatus 1 according to the embodiment described above will be described.

Figure 8:
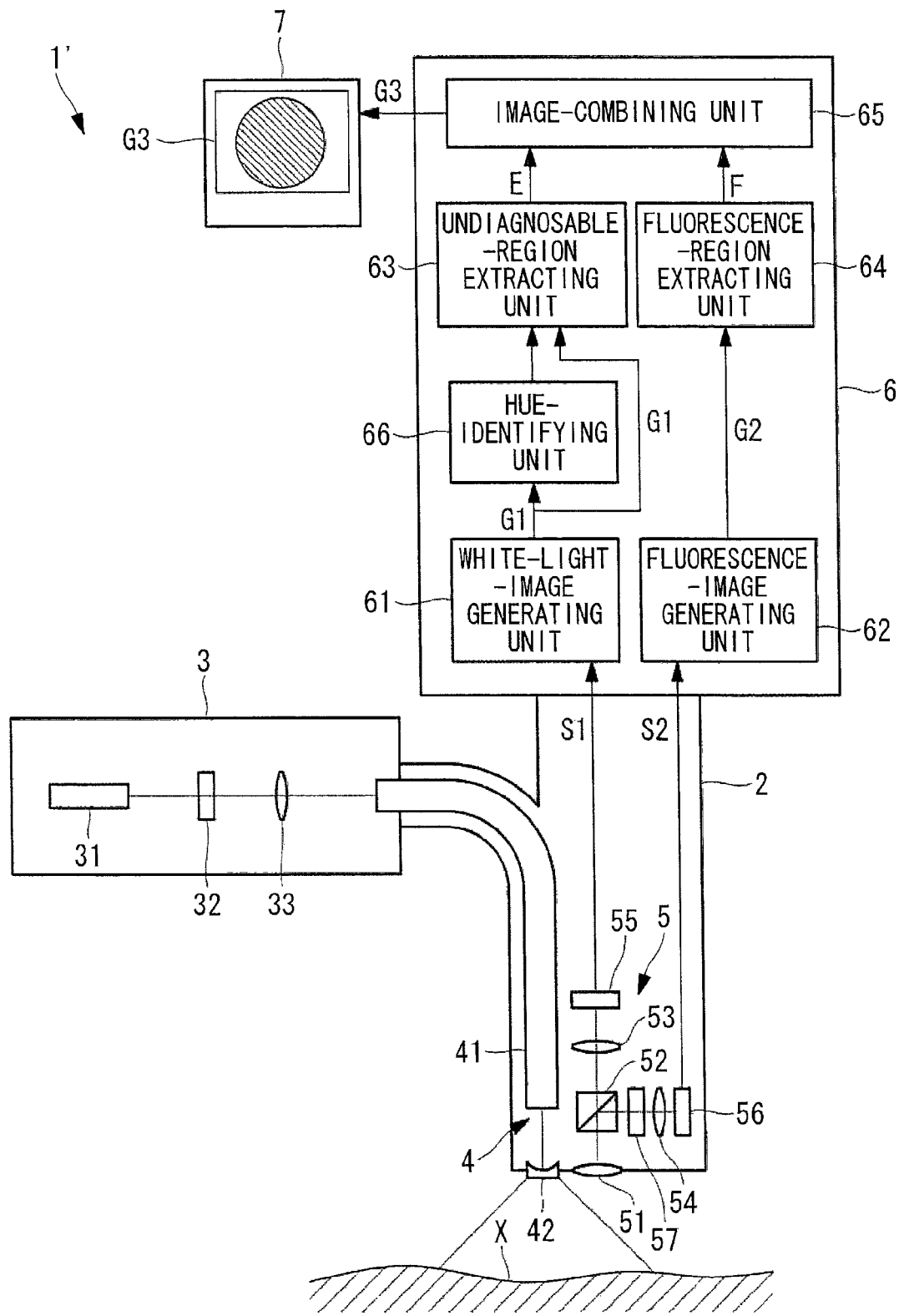
FIG. 8 is an overall block diagram showing a modification of the fluoroscopy apparatus in FIG. 1.

The fluoroscopy apparatus 1 sets the luminance of a white-light image G1 corresponding to the detection limit Lim of the imaging device 56 as the predetermined detection limit threshold and extracts a region with luminances at or below the detection limit threshold as an undiagnosable region E. A fluoroscopy apparatus 1' according to this modification differs from the fluoroscopy apparatus 1 in that, instead of or in addition to setting the detection limit threshold in the above manner, a predetermined visibility limit threshold is set for each position in the white-light image G1 depending on the hue at that position. Specifically, as shown in FIG. 8, the image processor 6 of the fluoroscopy apparatus 1' includes a hue-identifying unit 66 that identifies the hue of each pixel of the white-light image G1.

This modification also uses the following method as the method for generating a combined image G3. Specifically, the imaging device 55 includes three types of photoreceptors sensitive to red, green, and blue light, respectively, in white light. The white-light-image generating unit 61 generates R, G, and B images colored in red, green, and blue pseudo colors from image information acquired by the respective photoreceptors and outputs these three monochrome images to the image-combining unit 65.

The image-combining unit 65 colors the fluorescence region F input from the fluorescence-region extracting unit 64 in the green pseudo color and adds the signals of the fluorescence region F to the same positions in the G image to generate a G' image. The image-combining unit 65 then superimposes the R, G', and B images on top of each other to generate a color combined image G3. In the combined image G3, the fluorescence region F is displayed as a bright green region.

The hue-identifying unit 66 calculates the ratio of the luminances of each pixel of the white-light image G1 in the R, G, and B images and, based on the calculated ratio, determines to which of a plurality of hue regions set in advance the hue of that pixel belongs.

The undiagnosable-region extracting unit 63 sets a visibility limit threshold for each pixel depending on the hue region of that pixel identified by the hue-identifying unit 66. For example, if the fluorescence region F is displayed in green, as described above, a lower visibility limit threshold is set for a pixel with a hue belonging to the red hue region, and a higher visibility limit threshold is set for a pixel with a hue belonging to the yellow or white hue region.

Figure 9:
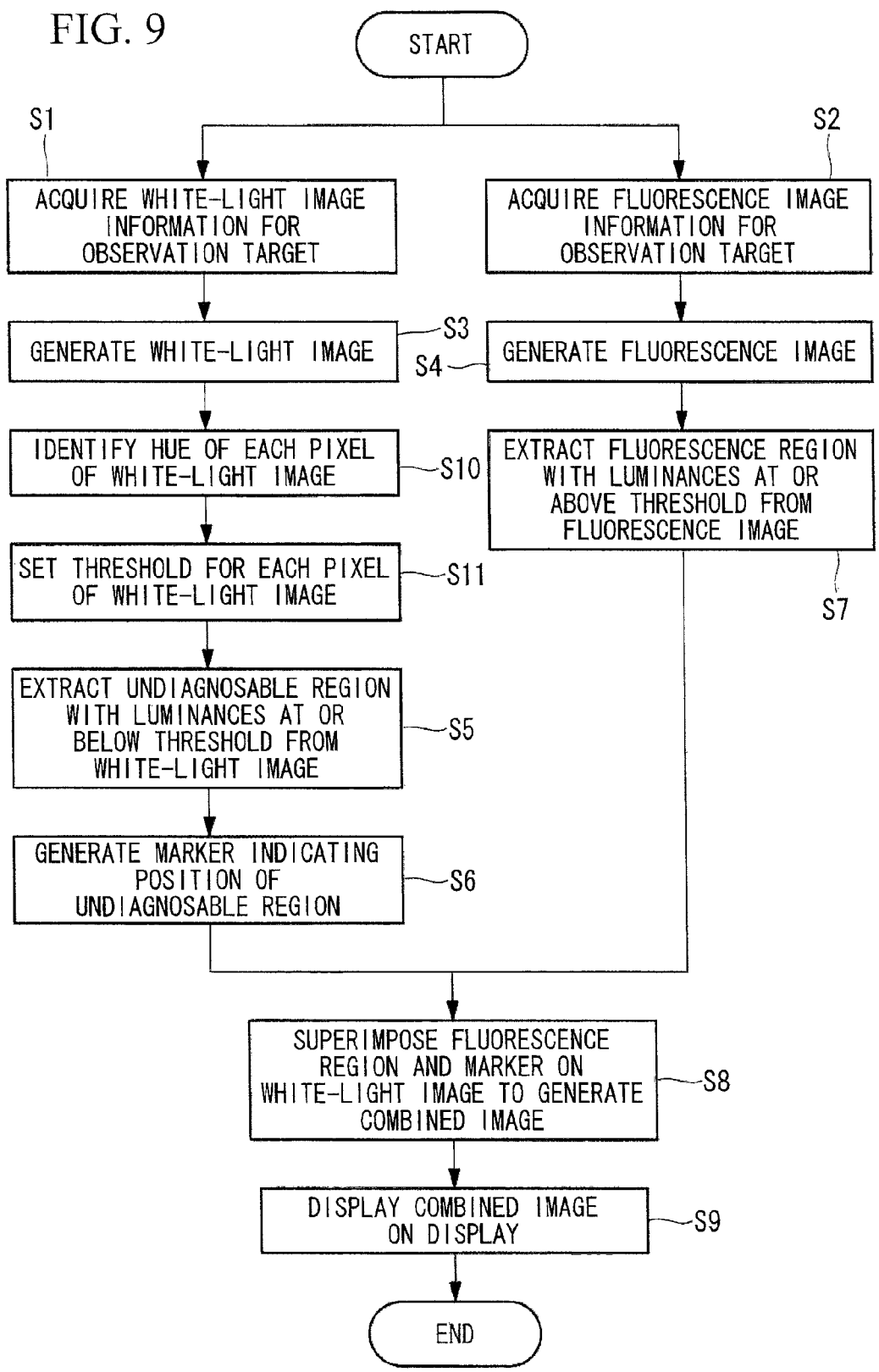
FIG. 9 is a flowchart illustrating the operation of the fluoroscopy apparatus in FIG. 8.

Next, a process by which the fluoroscopy apparatus 1' according to this modification generates a combined image G3 will be described with reference to the flowchart in FIG. 9.

When the fluoroscopy apparatus 1' generates a white-light image G1 in step S3, the hue-identifying unit 66 identifies the hue of each pixel of the white-light image G1 (step S10). The undiagnosable-region extracting unit 63 then sets a visibility limit threshold for each pixel depending on the hue of that pixel (step S11).

If the hue of the body tissue in the background of the fluorescence region F is red, the hue of the fluorescence region F and the hue of the body tissue contrast with each other. In this case, the user can easily recognize the fluorescence region F even if the luminance of the fluorescence region F is relatively low in the combined image G3. If the hue of the body tissue is yellow or white, the hue of the fluorescence region F and the hue of the body tissue are similar to each other. In this case, the user has difficulty in recognizing the fluorescence region F even if the luminance of the fluorescence region F is relatively high in the combined image G3. Thus, the visibility of the fluorescence region F depends not only on the luminance of the fluorescence region F, but also on the contrast between the hue of the fluorescence region F and the hue of the background. In step S11, the undiagnosable-region extracting unit 63 sets a higher visibility limit threshold for a pixel with a hue similar to the hue of the fluorescence region F and a lower visibility limit threshold for a pixel with a hue that contrasts with the hue of the fluorescence region F.

Next, in step S5, a region in the fluorescence image G2 corresponding to a fluorescence region F with insufficient luminance is extracted as an undiagnosable region E from the white-light image G1. It should be noted, however, that a region corresponding to a fluorescence region F where the hue of the tissue in the background is red is extracted as an undiagnosable region E only if the luminance is relatively low, and a region corresponding to a fluorescence region F where the hue of the tissue in the background is yellow or white is extracted as an undiagnosable region E even if the luminance is relatively high. Next, in step S6, a marker indicating the fluorescence region F extracted as an undiagnosable region E in step S5 is generated.

Thus, this modification displays a marker indicating a fluorescence region F that is difficult for the user to recognize because it is displayed in the combined image G3 but with low luminance and in a hue similar to that of the tissue in the background. This provides the advantage of ensuring that the user can recognize such a fluorescence region F, thereby assisting in more accurate diagnosis by the user.

Although the above embodiment and the modification thereof notify the user whether the undiagnosable-region extracting unit 63 has extracted an undiagnosable region E by displaying and not displaying a marker M in the combined image G3, sound changes may be used instead. Specifically, such a fluoroscopy apparatus includes a speaker that outputs sound and changes the pitch, rhythm, or volume of the sound output by the speaker or switches on and off the sound depending on whether an undiagnosable region E has been extracted. This ensures that the user is notified that there is an undiagnosable region E.

The pitch, rhythm, or volume of the sound may also be changed as the undiagnosable region E is moved in the white-light image G1 by manipulating the distal end 2a of the insertion part 2 to notify the user about the positional relationship between the undiagnosable region E and the distal end 2a of the insertion part 2 so that the user can easily guide the distal end 2a of the insertion part 2 toward the undiagnosable region E according to sound changes.

Figure 10:
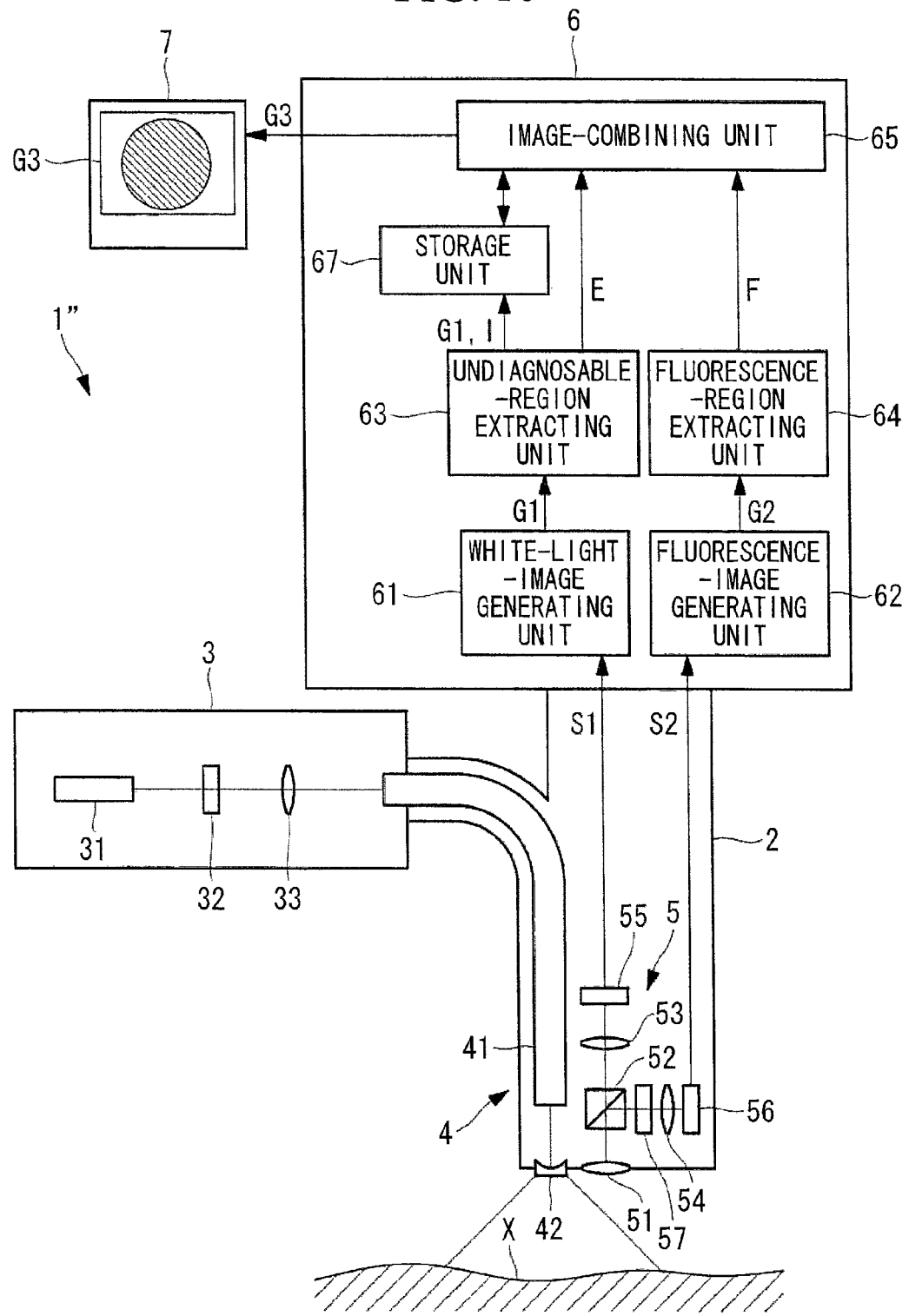
FIG. 10 is an overall block diagram showing another modification of the fluoroscopy apparatus in FIG. 1.

In the above embodiment and the modification thereof, as shown in FIG. 10, the image processor 6 may include a storage unit 67 that stores a white-light image G1 if an undiagnosable region E is extracted from the white-light image G1 by the undiagnosable-region extracting unit 63, and the image-combining unit 65 may be configured such that, each time an undiagnosable region E is input, the image-combining unit 65 checks for a match between the white-light image G1 from which the undiagnosable region E has been extracted and the white-light image G1 stored in the storage unit 67 and, if there is a matching white-light image G1 in the storage unit 67, stops generating a marker M indicating the undiagnosable region E or changes the marker M. The fluoroscopy apparatus 1" illustrated in FIG. 10 is based on the fluoroscopy apparatus 1.

If a marker M indicating the undiagnosable region E that has already been checked is repeatedly displayed to the user when the user examines the observation target X while moving the field of view, the user might feel irritated or check the same undiagnosable region E again. Accordingly, the usability can be improved if the user is no longer notified about an undiagnosable region E about which the user has already been notified.

In this embodiment, the predetermined detection limit threshold of the undiagnosable-region extracting unit 63 may be set based on insertion part information. Specifically, such a fluoroscopy apparatus may include an insertion part 2 having an IC chip (not shown) that stores insertion part information and that is attachable to and detachable from the light source 3 and/or the image processor 6, and the light source 3 or the image processor 6 may include an insertion-part determining unit (not shown) that determines the insertion part information stored in the IC chip. Examples of insertion part information include information about the site to be the observation target X corresponding to the insertion part 2, the type of fluorescent substance, and the specifications of the optical system.

In this case, when the insertion part 2 is connected to the light source 3 or the image processor 6, the insertion-part determining unit reads the insertion part information stored in the IC chip and sends the insertion part information to the undiagnosable-region extracting unit 63. The undiagnosable-region extracting unit 63 has a table that associates insertion part information with predetermined detection limit thresholds and selects and sets the detection limit threshold corresponding to the insertion part information input from the insertion-part determining unit.

This eliminates the need for the user to set the detection limit threshold depending on the insertion part 2 used, thus improving the usability.

Next, a fluoroscopy system including the fluoroscopy apparatus 1 and a calibration device 10 that calibrates the detection limit threshold used by the fluoroscopy apparatus 1 will be described with reference to FIGS. 11 and 12.

Figure 11:
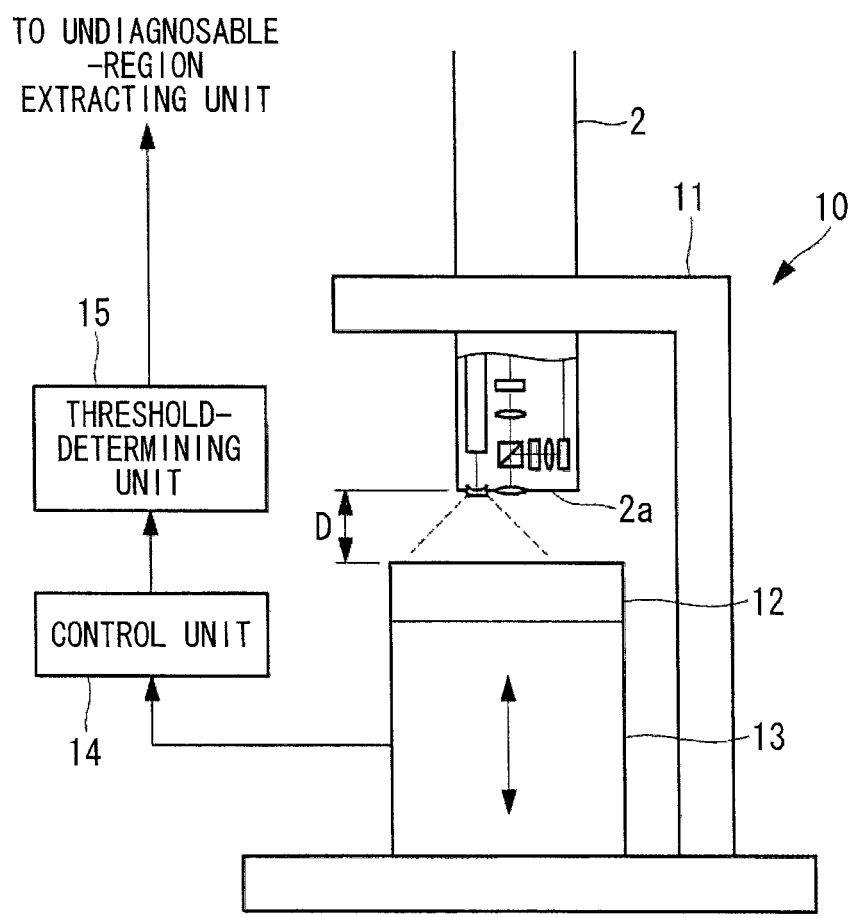
FIG. 11 is a block diagram showing a calibration device of a fluoroscopy system according to an embodiment of the present invention.

As shown in FIG. 11, the calibration device 10 according to this embodiment includes a holder 11 that holds the insertion part 2, a standard sample 12 disposed opposite the distal end 2a of the insertion part 2 held by the holder 11 at an observation distance D, a stage (light-intensity adjusting unit) 13 that changes the observation distance D between the distal end 2a of the insertion part 2 and the standard sample 12, a control unit 14 that controls the stage 13, and a threshold-determining unit 15 that determines the detection limit threshold based on the luminances of white-light images G1 and fluorescence images G2 acquired at different observation distances D.

The standard sample 12 has an examination surface with a uniform structure opposite the distal end 2a of the insertion part 2 so that it uniformly reflects white light and uniformly emits fluorescence over the entire examination surface.

The control unit 14 actuates the stage 13 to change the observation distance D stepwise and outputs the observation distance D to the threshold-determining unit 15 each time the observation distance D is changed. Upon receiving the observation distance D from the control unit 14, the threshold-determining unit 15 receives a white-light image G1 and a fluorescence image G2 generated at that observation distance D from the white-light-image generating unit 61 and the fluorescence-image generating unit 62, respectively.

In this manner, the threshold-determining unit 15 obtains data that associates the observation distance D with the luminances of the white-light images G1 and the fluorescence images G2. FIG. 12 shows a graph showing the relationship between the observation distance D and the luminance Vw of the white-light images G1 and the luminance Vf of the fluorescence images G2 obtained by the threshold-determining unit 15.

Figure 12:
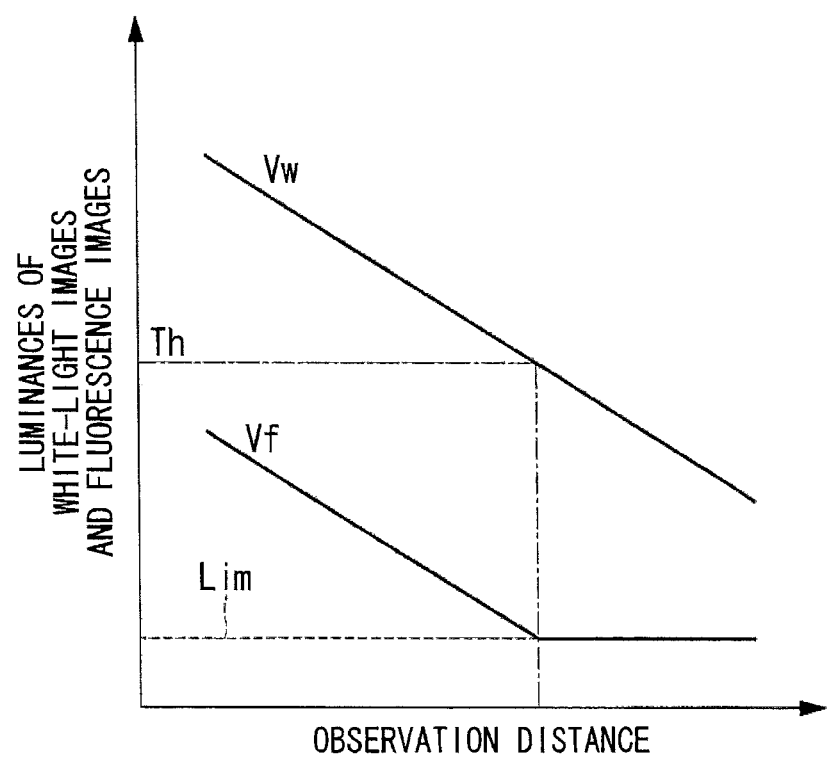
FIG. 12 is a graph showing the relationship between the observation distance and the luminance of white-light images and the luminance of fluorescence images obtained by the calibration device in FIG. 11.

As shown in FIG. 12, the luminance Vw of the white-light images G1 and the luminance Vf of the fluorescence images G2 both vary inversely with the observation distance D. The white-light images G1 acquired from white light, which has sufficient intensity, have sufficient luminances Vw in the range of sufficiently large observation distances D. The fluorescence images G2 acquired from fluorescence, which is weaker than white light, have a constant level of luminance Vf in the range of observation distances D where white light has sufficient intensity because the fluorescence intensity falls below the detection limit Lim of the imaging device 56. The threshold-determining unit 15 determines the detection limit threshold Th as the luminance Vw of the white-light images G1 at the observation distance D at which the luminance Vf of the fluorescence images G2 rises, and sets the thus-determined detection limit threshold Th in the undiagnosable-region extracting unit 63.

In the calibration device 10 according to this embodiment, instead of the control unit 14 controlling the stage 13 to change the observation distance D, the light source (light-intensity adjusting unit) 3 may be controlled to change the intensity of the white light and excitation light emitted toward the standard sample 12.

Thus, the relationship between the luminance Vw of white-light images and the luminance Vf of fluorescence images, shown in FIG. 12, is obtained, and the detection limit threshold Th can be similarly determined.

REFERENCE SIGNS LIST 1 fluoroscopy apparatus
2 insertion part
2a distal end
3 light source (light-intensity adjusting unit)
31 xenon lamp
32 filter
33 coupling lens
4 illumination unit
41 light-guide fiber
42 illumination optical system
5 imaging unit
51 objective lens
52 dichroic mirror
53, 54 condenser lens
55, 56 imaging device
57 excitation-light-cut filter
6 image processor
61 white-light-image generating unit (reference-image generating unit)
62 fluorescence-image generating unit
63 undiagnosable-region extracting unit (determining unit, extracting unit)
64 fluorescence-region extracting unit
65 image-combining unit (notifying unit)
66 hue-identifying unit
67 storage unit
7 display
10 calibration device
11 holder
12 standard sample
13 stage (light-intensity adjusting unit)
14 control unit
15 threshold-determining unit
X observation target
G1 white-light image (reference image)
G2 fluorescence image
G3 combined image
E undiagnosable region
F fluorescence region
M marker

The invention claimed is:

1. A fluoroscopy apparatus comprising:
a light source that irradiates an observation target with reference light and excitation light;
a fluorescence-image generating unit that captures fluorescence emitted from the observation target irradiated with the excitation light from the light source to generate a fluorescence image;
a reference-image generating unit that captures return light returning from the observation target irradiated with the reference light from the light source to generate a reference image;
an image-combining unit that superimposes the fluorescence image generated by the fluorescence-image generating unit on the reference image generated by the reference-image generating unit to generate a combined image;

a determining unit that compares a luminance at each position in the reference image generated by the reference-image generating unit with a predetermined threshold to determine whether there is a position with a luminance at or below the predetermined threshold;

a notifying unit that, if the determining unit determines that there is a position with a luminance at or below the predetermined threshold, provides notification thereof; and a hue-identifying unit that identifies the hue at each position in the reference image generated by the reference-image generating unit, wherein the image-combining unit colors the fluorescence image in a predetermined hue and superimposes the fluorescence image on the reference image, and wherein the determining unit sets a visibility limit threshold as the predetermined threshold for each position in the reference image depending on the contrast between the predetermined hue and the hue identified by the hue-identifying unit.

2. The fluoroscopy apparatus according to claim 1, wherein the fluorescence-image generating unit includes an imaging device that captures the fluorescence, and the determining unit has a detection limit threshold as the predetermined threshold, the detection limit threshold being the luminance of a reference image capturing return light having an intensity corresponding to a fluorescence intensity equal to a detection limit of the imaging device for the fluorescence.

3. A fluoroscopy system comprising:

the fluoroscopy apparatus according to claim 2; and a calibration device that calibrates the detection limit threshold used by the determining unit, wherein the calibration device includes
- a standard sample that emits fluorescence and return light when irradiated with the excitation light and the reference light from the light source;
- a light-intensity adjusting unit that changes the intensities of the excitation light and the reference light with which the standard sample is irradiated; and
- a threshold-determining unit that determines the detection limit threshold based on the relationship between the luminances of a plurality of reference images and a plurality of fluorescence images generated by capturing fluorescence and return light when the standard sample is irradiated with excitation light and reference light with different intensities by the light-intensity adjusting unit and that sets the detection limit threshold in the determining unit.

4. The fluoroscopy apparatus according to claim 1, further comprising an extracting unit that extracts the position determined to have a luminance at or below the predetermined threshold by the determining unit, wherein the notifying unit provides notification of the position extracted by the extracting unit.

5. The fluoroscopy apparatus according to claim 4, wherein the notifying unit displays a marker indicating the position extracted by the extracting unit on the combined image.

6. The fluoroscopy apparatus according to claim 5, wherein the determining unit has a plurality of predetermined thresholds, and the notifying unit displays the marker on the combined image in a different display form depending on to which of a plurality of ranges defined by the plurality of predetermined thresholds the luminance of the position determined to have a luminance at or below the predetermined thresholds by the determining unit belongs.

7. The fluoroscopy apparatus according to claim 1, wherein the notifying unit provides the notification by changing an output sound.

8. A fluoroscopy apparatus comprising:

a light source that irradiates an observation target with reference light and excitation light;

a fluorescence-image generating unit that captures fluorescence emitted from the observation target irradiated with the excitation light from the light source to generate a fluorescence image;

a reference-image generating unit that captures return light returning from the observation target irradiated with the reference light from the light source to generate a reference image;

an image-combining unit that superimposes the fluorescence image generated by the fluorescence-image generating unit on the reference image generated by the reference-image generating unit to generate a combined image;

a determining unit that compares a luminance at each position in the reference image generated by the reference-image generating unit with a predetermined threshold to determine whether there is a position with a luminance at or below the predetermined threshold;

a notifying unit that, if the determining unit determines that there is a position with a luminance at or below the predetermined threshold, provides notification thereof; and a storage unit that stores the position in the reference image determined to have a luminance at or below the predetermined threshold by the determining unit in association with the reference image, wherein the notifying unit checks for a match between a reference image determined to contain a position with a luminance at or below the predetermined threshold by the determining unit and the reference image stored in the storage unit and, if the storage unit stores a matching reference image, stops providing notification.

9. The fluoroscopy apparatus according to claim 8, wherein the fluorescence-image generating unit includes an imaging device that captures the fluorescence, and the determining unit has a detection limit threshold as the predetermined threshold, the detection limit threshold being the luminance of a reference image capturing return light having an intensity corresponding to a fluorescence intensity equal to a detection limit of the imaging device for the fluorescence.

10. A fluoroscopy system comprising:

the fluoroscopy apparatus according to claim 9; and a calibration device that calibrates the detection limit threshold used by the determining unit, wherein the calibration device includes
- a standard sample that emits fluorescence and return light when irradiated with the excitation light and the reference light from the light source;
- a light-intensity adjusting unit that changes the intensities of the excitation light and the reference light with which the standard sample is irradiated; and
- a threshold-determining unit that determines the detection limit threshold based on the relationship between the luminances of a plurality of reference images and a plurality of fluorescence images generated by capturing fluorescence and return light when the standard sample is irradiated with excitation light and reference light with different intensities by the light-intensity adjusting unit and that sets the detection limit threshold in the determining unit.

11. The fluoroscopy apparatus according to claim 8, further comprising an extracting unit that extracts the position determined to have a luminance at or below the predetermined threshold by the determining unit,
   wherein the notifying unit provides notification of the position extracted by the extracting unit.

12. The fluoroscopy apparatus according to claim 11, wherein the notifying unit displays a marker indicating the position extracted by the extracting unit on the combined image.

13. The fluoroscopy apparatus according to claim 12, wherein
   the determining unit has a plurality of predetermined thresholds, and
   the notifying unit displays the marker on the combined image in a different display form depending on to which of a plurality of ranges defined by the plurality of predetermined thresholds the luminance of the position determined to have a luminance at or below the predetermined thresholds by the determining unit belongs.

14. The fluoroscopy apparatus according to claim 8, wherein the notifying unit provides the notification by changing an output sound.

* * * * *